United States Patent [19]
Yamauchi et al.

[11] Patent Number: 5,607,756
[45] Date of Patent: Mar. 4, 1997

[54] METHOD OF CORRECTION OF THE FOOT, SPLINT FOR USE IN PRACTICING THE METHOD, AND FOOTWEAR WITH THE SPLINT

[75] Inventors: Kiyoshi Yamauchi; Hiroyuki Yoshida; Atsushi Kita, all of Miyagi, Japan

[73] Assignee: Tokin Corporation, Miyagi, Japan

[21] Appl. No.: 430,757

[22] Filed: Apr. 27, 1995

[30] Foreign Application Priority Data

Apr. 28, 1994 [JP] Japan .................................. 6-090991

[51] Int. Cl.$^6$ .................................................. D03D 3/00
[52] U.S. Cl. ...................... 442/6; 12/1 G; 12/133 R; 36/44; 36/91; 36/145; 36/166; 36/169; 428/902; 602/5; 602/7; 602/23; 602/28; 602/66
[58] Field of Search ...................... 428/229, 231, 428/256, 258, 259, 902; 602/5, 7, 23, 28, 66; 12/1 G, 133; 36/91, 44, 145, 154, 166, 169

[56] References Cited

U.S. PATENT DOCUMENTS 4,572,196  2/1986  Prahl .
5,137,446  8/1992  Yamauchi et al. ...................... 433/20
5,190,546  3/1993  Jervis .
5,241,762  9/1993  Rosen ...................................... 36/97

FOREIGN PATENT DOCUMENTS 3517073  11/1986  Germany .
0118642   5/1989  Japan .
4-71501   3/1992  Japan .............................. A43B 23/02
4343845  11/1992  Japan .
1406723   9/1975  United Kingdom .

*Primary Examiner*—James J. Bell
*Attorney, Agent, or Firm*—Hopgood, Calimafde, Kalil & Judlowe

[57] ABSTRACT

A foot correction method comprises the steps of raising a plantar arch (15) and applying a pressure on either side of a foot (13) to thereby maintain a configuration of a longitudinal arch and a transversal arch of the foot (13) so as to prevent and correct a spraying phenomenon of the foot (13). A splint (11, 23) for practicing the method comprises shape memory alloy wires preferably in the form of either woven fabric, such as a mesh (17), or a nonwoven fabric plate. The shape memory alloy wires preferably consists of a Ti-Ni series alloy exhibiting superelasticity at a normal or used temperature.

24 Claims, 5 Drawing Sheets

METHOD OF CORRECTION OF THE FOOT, SPLINT FOR USE IN PRACTICING THE METHOD, AND FOOTWEAR WITH THE SPLINT

BACKGROUND OF THE INVENTION

This invention relates to a method of reinforcement or correction of the foot in order to prevent and cure a deformity of the foot such as a flatfoot and hallux valgus, a splint for use in practicing the method, and footwear with the splint.

Hallux valgus is a deformity of the foot, namely, a prominence of a joint at a root of a big toe towards the medial side of the foot. This results from a fall of a medial longitudinal arch, namely, a plantar arch which leads pronation or spraying phenomenon in which five toes are spread in a transversal direction. When footwear is put on, the prominence of the joint collides with the footwear to cause a pain. If the footwear does not well fit the foot, occurrence of the deformity is accelerated.

In view of the above, use is made of an arch support as a therapeutic or a corrective appliance to treat or cure the hallux valgus. The arch support is for raising the plantar arch in order to suppress the pronation. The arch support is generally used in the form of a supporter or an insole of a shoe.

The therapeutic or corrective appliance of the type described is generally made of fabric, leather, plastic, steel, or the like. These materials, however, have a problem in elasticity and in shape retentivity.

In addition, the therapeutic or corrective appliance is insufficient to suppress the spraying phenomenon in which the toes of the foot are spread in the transversal direction.

SUMMARY OF THE INVENTION

It is an object of this invention to provide a method of correction of the foot, which is excellent not only in performance but also in fitness, comfortableness, and appearance.

It is another object of this invention to provide a corrective appliance, namely, a splint for use in practicing the above-mentioned method of correction of the foot.

It is still another object of this invention to provide footwear with the above-mentioned splint.

It is a still further object of this invention to provide a foot protector with the above-mentioned splint.

A splint to which this invention is applicable is for reinforcement or correction of the foot in order to prevent and cure a deformity of the foot such as a flatfoot and hallux valgus. According to a first aspect of this invention, the splint comprises a lamina or a thin plate at least partially containing shape memory alloy wires and is formed into a desired shape in conformity with a part of the foot to which the splint is attached.

In the first aspect of this invention, the lamina or the thin plate comprises a mesh comprising warp and weft. At least one of the warp and the weft is adapted to comprise the shape memory alloy wires. It may be that one of the warp and the weft comprises the shape memory alloy wires while the other comprises synthetic macromolecule wires. Alternatively, both of the warp and the weft may comprise the shape memory alloy wires. In this case, the mesh may be coated with a synthetic macromolecule material.

According to this invention, the shape memory alloy wires are preferably made of a shape memory alloy selected from a Ti-Ni alloy and a Ti-Ni-X alloy (X being at least one selected from a group consisting of Fe, Cu, Cr, V, and Co) but may be a Cu-based alloy, Fe-based alloy, and so on.

As well known, the shape memory alloy such as the Ti-Ni alloy, the Ti-Ni-X alloy, and Cu-Zn-Al alloy exhibits a remarkable shape memory effect accompanying reverse transition of martensite. Among those, the Ti-Ni alloy and the Ti-Ni-X alloy are specially excellent in shape memory effect and superelasticity and therefore widely used as a shape memory element for an actuator in a ventilator, a microwave oven, an air conditioner, and the like and as a superelastic core element for a catheter guide wire, a brassiere, corsets, an antenna, or the like.

In the first aspect of this invention, the synthetic macromolecule material is preferably rich in elasticity, for example, a nylon series macromolecule material, a polyurethane series macromolecule material, and a polytetrafluoroethylene (Teflon) series macromolecule material.

It is noted here that a memory temperature (shape recovery temperature) of the Ti-Ni series shape memory alloy is determined by an alloy composition, a cold working rate, and a heat treatment temperature. According to this invention, it is essential that an initial shape is recovered at a normal or used temperature and that plantar and transversal arches are supported by superelasticity exhibited after recovery of the shape. It is sufficient that the shape memory alloy has a shape recovery temperature lower than the normal or used temperature. The Ti-Ni alloy should also have a martensite transformation start temperature not higher than the human body temperature after the Ti-Ni alloy is subjected to a heat treatment at a temperature not lower than a recrystallization temperature of the Ti-Ni alloy.

Specifically, the splint according to the first aspect of this invention recovers its shape at a normal internal temperature (30°–40° C.) inside a shoe and exhibits superelasticity after recovery of the shape to thereby press support the plantar arch and either side of the foot. In addition, a greater anti-spread force is obtained by a shape memory function against repetitive deformation and an increase of superelasticity with an increase of the internal temperature during walking. Thus, a greater effect is obtained.

The Ti-Ni series alloy exhibits superelasticity at the human body temperature when it is subjected to a heat treatment at a temperature between 400° C. and 500° C. after cold working of 30% or more.

According to a second aspect of this invention, there is provided a method of correction of the foot, comprising the steps of preparing the above-mentioned splint, forming the splint into a shape corresponding to a configuration of a desired part of the foot to be corrected, and attaching the splint to the desired part. In the second aspect of this invention, it is preferable to repeat attachment and removal of the lamina or the thin plate.

In the method of correction of the foot, the lamina or the thin plate raises the plantar arch and applies a pressure on either side of the foot to maintain a configuration of a longitudinal arch and a transversal arch of the foot so as to prevent and correct the spraying phenomenon of the foot.

According to a third aspect of this invention, there is provided a foot protector having the above-mentioned splint. It is noted here that, in this invention, the foot protector includes a supporter, socks, Japanese socks, tights, stockings, and the like. The splint is attached to the foot protector in any appropriate manner, for example, sewing or sticking, inasmuch as the splint is fixed to the foot protector.

According to a fourth aspect of this invention, there is provided footwear having the above-mentioned splint.

In the fourth aspect of this invention, the footwear includes various objects fitted to the foot, such as shoes, high-heel shoes, galoshes, boots, sandals, Japanese sandals, slippers, casuals, moccasins, and mules. The splint is attached to the footwear in any appropriate manner. For example, the splint may be contained in the shoe, adhered to the shoe, or tacked to the shoe. The splint may be attached to the sock by sewing or adhesion.

DESCRIPTION OF THE PREFERRED EMBODIMENTS

Figure 1:
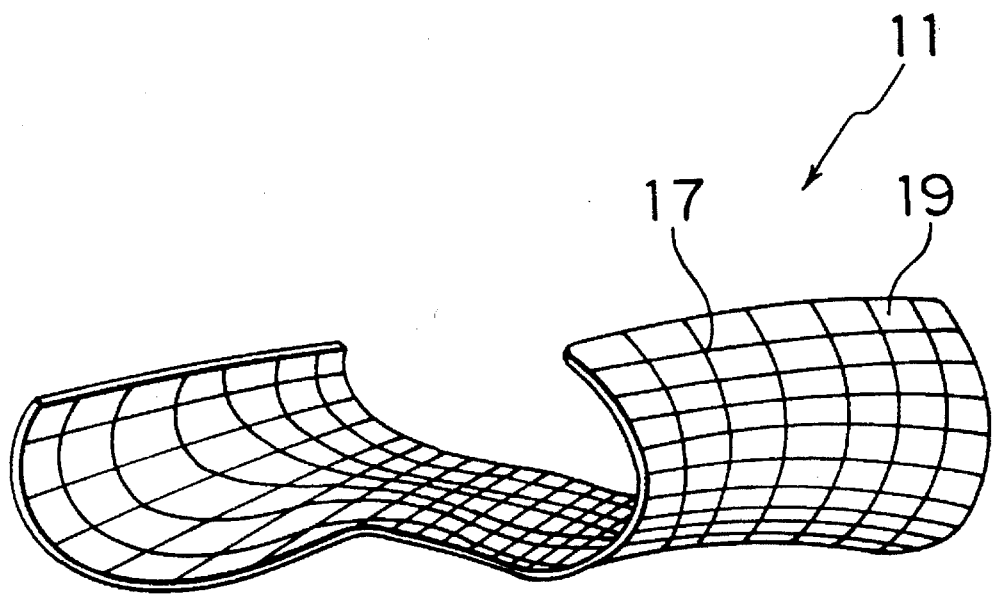
FIG. 1 is a perspective view of a splint according to a first embodiment of this invention for attachment to a plantar arch of the foot.

Now, description will be made as regards embodiments of this invention with reference to the drawing.

Figure 2:
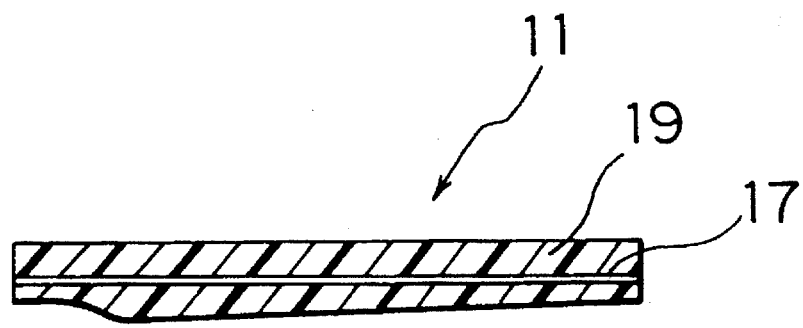
FIG. 2 is a sectional view of the splint illustrated in FIG. 1.
Figure 3:
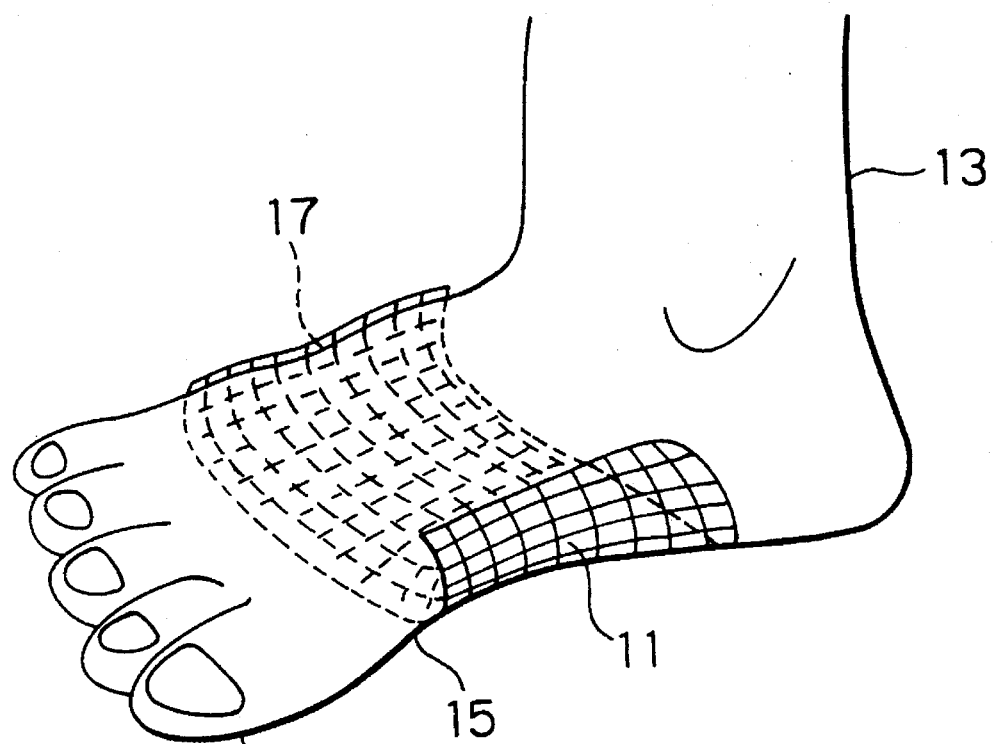
FIG. 3 shows the splint illustrated in FIGS. 1 and 2 which is attached to the plantar arch.

FIGS. 1 through 3 show a first embodiment of this invention.

Referring to FIGS. 1 through 3, a splint 11 according to the first embodiment has a structure adapted for attachment to a plantar arch 15 of a foot 13. The splint 11 raises the plantar arch 15 and applies a pressure on either side of the foot 13 to thereby maintain a configuration of a longitudinal arch and a transversal arch of the foot 13 so as to prevent and correct a spraying phenomenon of the foot 13 described in the foregoing. The splint 11 comprises a mesh 17 made of a shape memory alloy and coated with a synthetic resin material 19. A reference numeral 21 represents a big toe. The splint 11 illustrated in FIGS. 1 and 2 is manufactured in the manner which will presently be described.

The mesh 17 made of a Ti-Ni alloy wire consisting of 49 at % Ti and 51 at % Ni is cut into a shape corresponding to a configuration of the plantar arch 15 of the foot 13. The mesh 17 is tightly and fixedly fitted onto a foot-shaped mold made of plaster which is not shown in the figure. Then, the mesh 17 is subjected to a heat treatment at a temperature between 400° C. and 500° C. to fix the shape of the mesh 17. The mesh 17 heat-treated as described above acts as a reinforcing member exhibiting superelasticity at a normal or used temperature (between 30° C. and 40° C.).

Then, the mesh 17 is coated with the synthetic resin material (urethane) 19. Thereafter, the mesh 17 is cut into a shape illustrated in FIG. 1. Cut ends are again coated with the synthetic resin material 19. Thus, the splint 11 is formed.

Figure 4:
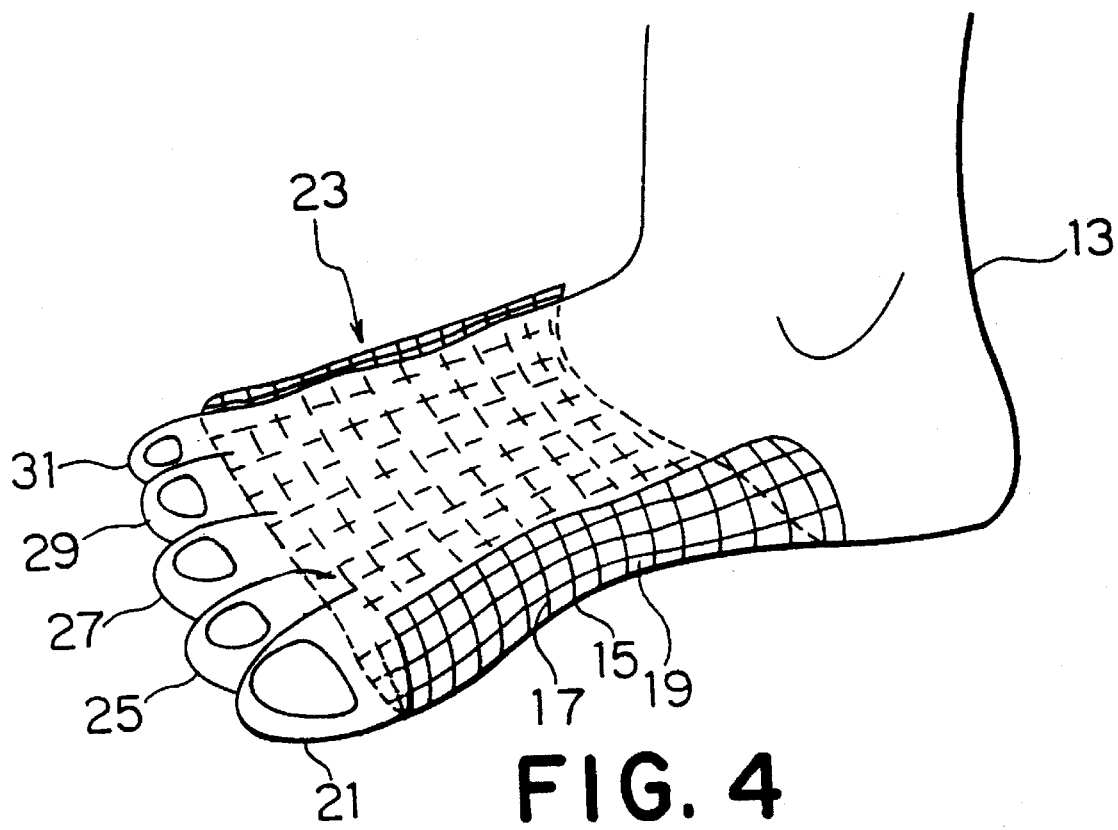
FIG. 4 is a perspective view of a splint according to another embodiment of this invention which is attached to a wider area including a big toe.
Figure 5:
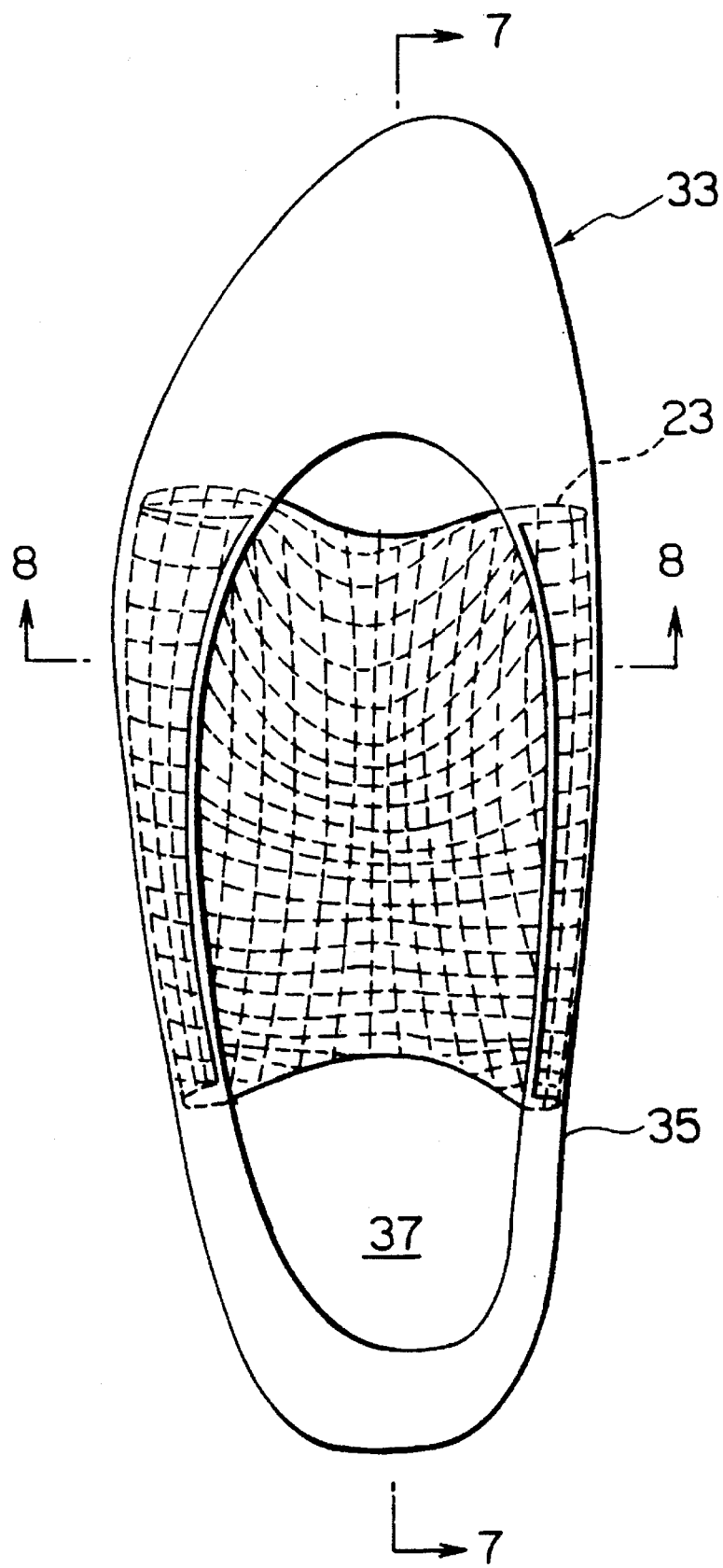
FIG. 5 is a plan view of a high-heel shoe with the splint in FIG. 4 attached thereto.
Figure 6:
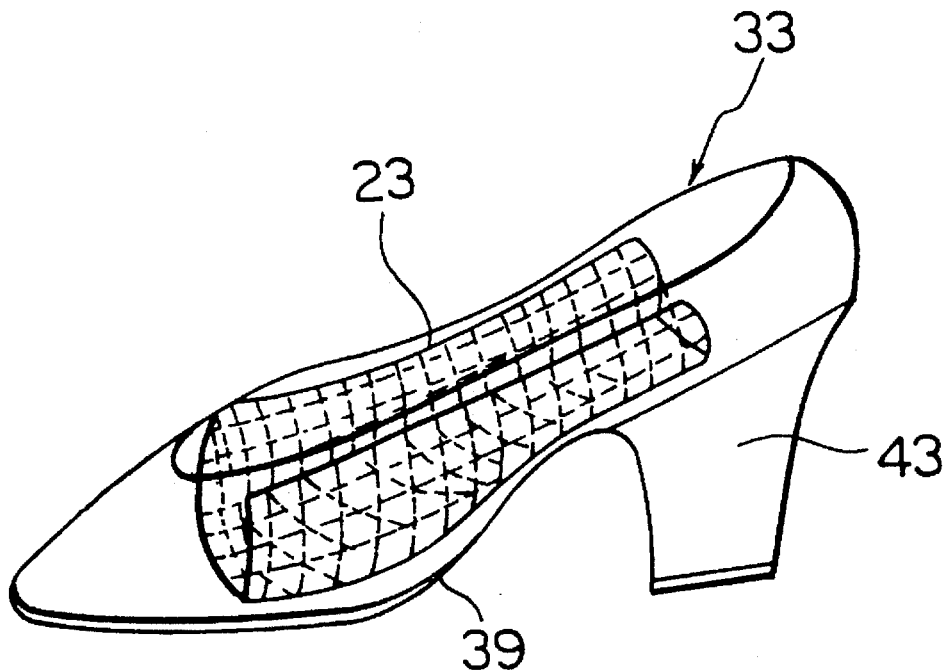
FIG. 6 is a side view of the high-heel shoe illustrated in FIG. 5.
Figure 7:
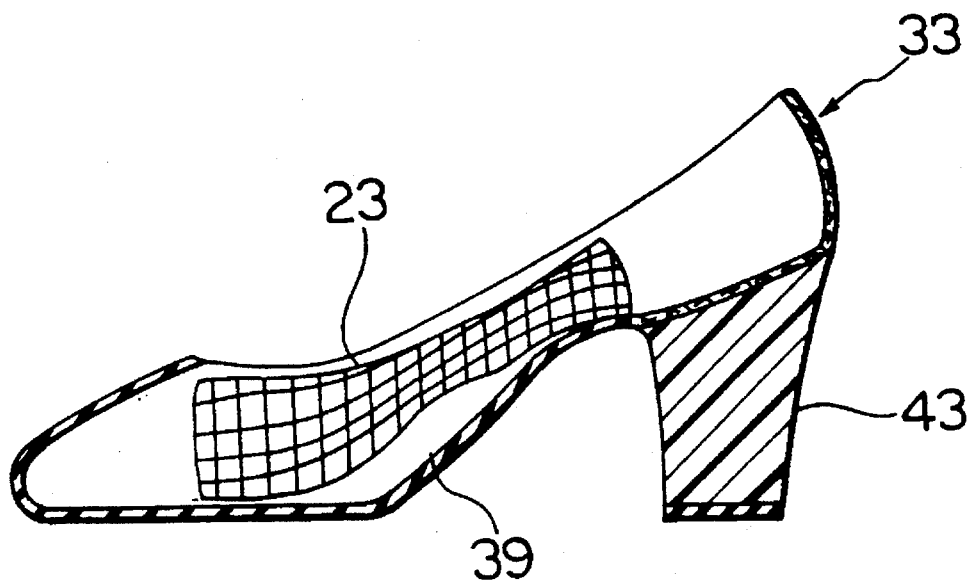
FIG. 7 is a sectional view taken along a line 7—7 in FIG. 5.
Figure 8:
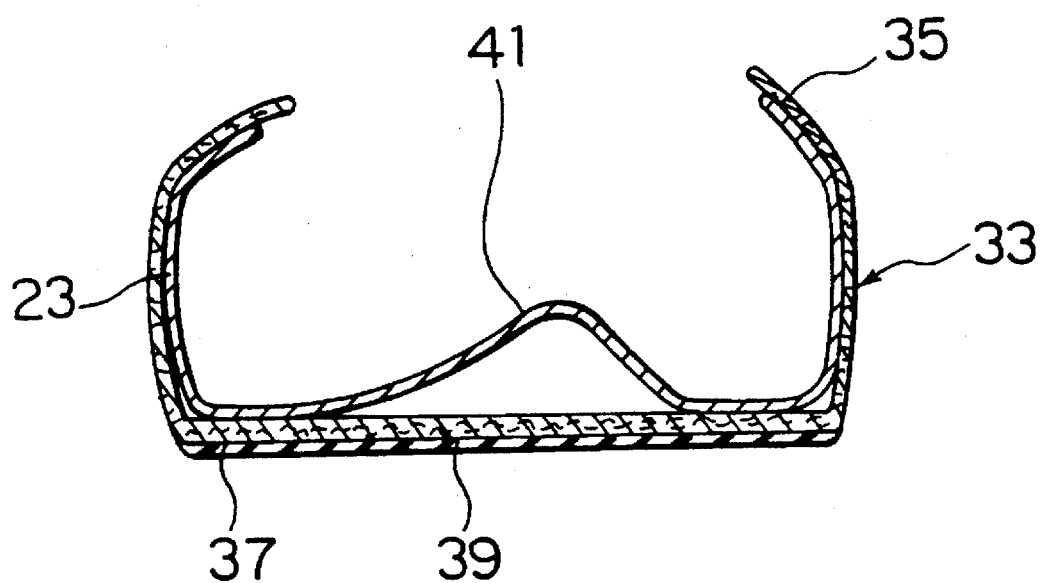
FIG. 8 is a sectional end view taken along a line 8—8 in FIG. 5.

Next referring to FIG. 4, a splint 23 according to another embodiment of this invention will be described. As illustrated in FIG. 4, the splint 23 according to this embodiment is similar to that of the foregoing embodiment except that the splint 23 is attached to a wider area ranging from the plantar arch 15 to a big toe 21 of the foot 13. In the second embodiment, the splint 23 may have a structure such that the big toe 21 alone is covered while the other toes 25, 27, 29, and 31 are uncovered and exposed. Like the foregoing embodiment, the splint 23 of this embodiment is manufactured as follows. The mesh 17 is molded into a shape corresponding to the foot-shaped mold, cut, subjected to heat treatment, coated by the urethane resin material 19, cut, and again coated at the cut ends.

In order to know an adaptability for use as the splint of this invention, various kinds of shape memory alloys were tested for a relationship among alloy compositions, characteristics, and repetitive recovery life.

Table 1 shows alloy samples each of which was subjected to a heat treatment at a temperature not lower than its recrystallization temperature. The alloy samples had martensite transformation start temperatures (Ms) different from one another. Each alloy sample was subjected to measurement of a superelasticity start temperature and a repetitive recovery test with a variation of a cold working rate and a heat treatment temperature after cold working. The results of the tests are also shown in Table 1.

As shown in Table 1, Ti-Ni alloy samples (Nos. 12, 13, and 14) had the martensite transformation start temperatures (Ms) higher than 37° C. Among those, the sample No. 14 had a superelasticity start temperature lower than the human body temperature by lowering the heat treatment temperature after cold working. However, because of such an insufficient heat treatment, it was difficult to fix the shape. Taking the above into consideration, the heat treatment was carried out at 450° C. in the samples Nos. 12 and 13. In these samples, however, no superelasticity was exhibited at the human body temperature.

TABLE 1

| Sample No. | Alloy Composition | Ms (°C.) | Cold Working Rate | Heat Treatment Temperature (°C.) × 30 min. | Pseudo Elasticity Start Temperature | Repetitive Recovery Life |
|---|---|---|---|---|---|---|
| 1 | $Ti_{49}Ni_{51}$ | −10 | 20 | 400 | −5 | x |
| 2 | $Ti_{49}Ni_{51}$ | −10 | 30 | 400 | −15 | o |
| 3 | $Ti_{49}Ni_{51}$ | −10 | 40 | 400 | −20 | o |
| 4 | $Ti_{49}Ni_{51}$ | −10 | 40 | 350 | −30 | o* |
| 5 | $Ti_{49}Ni_{51}$ | −10 | 40 | 500 | 5 | o |
| 6 | $Ti_{49}Ni_{51}$ | −10 | 40 | 550 | 10 | o |
| 7 | $Ti_{49}Ni_{51}$ | −10 | 40 | 600 | 10 | Δ |

TABLE 1-continued

| Sample No. | Alloy Composition | Ms (°C.) | Cold Working Rate | Heat Treatment Temperature (°C.) × 30 min. | Pseudo Elasticity Start Temperature | Repetitive Recovery Life |
|---|---|---|---|---|---|---|
| 8 | $Ti_{49}Ni_{51}$ | −10 | 40 | 650 | 10 | x |
| 9 | $Ti_{49}Ni_{51}$ | 37 | 40 | 450 | 30 | o |
| 10 | $Ti_{49.8}Ni_{50.2}$ | 20 | 40 | 450 | 10 | o |
| 11 | $Ti_{49.5}Ni_{50.2}V_{0.3}$ | −5 | 40 | 450 | −10 | o |
| 12 | $Ti_{50}Ni_{50}$ | 50 | 40 | 450 | 40 | — |
| 13 | $Ti_{49.9}Ni_{50.1}$ | 40 | 40 | 450 | 38 | — |
| 14 | $Ti_{50}Ni_{50}$ | 50 | 40 | 300 | 0 | Δ* |

\* it is difficult to fix the shape
x deteriorated within 50 times of repetition
Δ deteriorated within 100 times of repetition
o not deteriorated beyond 100 times of repetition On the other hand, each of the samples Nos. 1 through 8 had the martensite transformation start temperatures (Ms) equal to −10° C. Among those, the sample No. 1 had short repetitive recovery life because of insufficient cold working. Even if cold working is as sufficient as 40%, repetitive recovery life was similarly short in the samples Nos. 7 and 8 in which the heat treatment temperature was as high as 600° C. or more. Accordingly, the samples Nos. 2, 3, 5, and 6 are preferable. In view of the martensite transformation start temperature (Ms) and the repetitive recovery life, the samples Nos. 9, 10, and 11 are preferable also.

Next, woven fabric comprising a combination of the shape memory alloy wires and polytetrafluoroethylene (Teflon) wires was prepared and subjected to a repetitive recovery life test as follows.

The Ti-Ni alloy consisting of 49 at % Ti and 51 at % Ni was subjected to cold working at a rate of 30% to obtain the alloy wire having a diameter of 0.5 mm. The alloy wire and a polytetrafluoroethylene (Teflon) green material (before firing) were used as warp (longitudinal filaments) and weft (transversal filaments), respectively, to obtain a blended woven sheet. The blended woven sheet was subjected to a heat treatment at a temperature between 200° C. and 600° C. Then, compactibility of the sheet was examined. The result is shown in Table 2 as samples Nos. 15 through 19.

As shown in Table 2, the sample (No. 15) subjected to a heat treatment at a temperature lower than 400° C. was difficult to fix the shape, as in the first the embodiment. On the other hand, the sample (No. 19) subjected to a heat treatment at a temperature higher than 550° C. could not be used because of occurrence of thermal decomposition of polytetrafluoroethylene (PTFE).

TABLE 2

| Sample No. | Material of Blended Woven Fabric | | Heat Treatment | |
|---|---|---|---|---|
| | Longitudinal Filament | Transversal Filament | Temperature (°C.) × 30 min. | Compactibility |
| 15 | $Ti_{49}Ni_{51}$ | PTFE | 200 | shape unfixable |
| 16 | $Ti_{49}Ni_{51}$ | | 400 | firing of PTFE insufficient, shape fixable |
| 17 | $Ti_{49}Ni_{51}$ | | 500 | shape fixable, no problem in firing of PTFE |
| 18 | $Ti_{49}Ni_{51}$ | | 550 | shape fixable, partial thermal decomposition of PTFE |
| 19 | $Ti_{49}Ni_{51}$ | | 600 | thermal decomposition of PTFE, unusable |

Referring to FIGS. 5 through 8, a high-heel shoe 33 comprises an upper 35, a sole 37, a rubber sole 39 outside and under the sole 37, and a heel 43. The splint 23 illustrated in FIG. 4 is attached to the inside of the high-heel shoe 33 so that a center portion 41 protrudes from the sole 37. With this structure, it is possible to correct the foot by simply putting on the high-heel shoe 33 without being noticed by others that the splint is used.

Although not described in the foregoing embodiments, the splint as an appliance for correction of the hallux valgus according to this invention can be preliminarily contained in footwear such as shoes on the market. Alternatively, the splint can be adhered to a foot protector such as socks.

As described above, the splint for correction of the hallux valgus according to this invention has a reduced thickness and does not essentially require a string or a strap. Accordingly, the splint can easily be attached and is excellent in appearance. As far as the shoes are put on, no one can know that the splint is used in the shoes.

What is claimed is:

1. A splint for reinforcement or correction of the foot in order to prevent and cure a deformity of the foot such as a flatfoot and hallux valgus, said splint comprising a lamina or a thin plate at least partially containing shape memory alloy wires and being formed into a desired shape in conformity with a configuration of a part of said foot to which said splint to which said splint is attached, wherein said lamina or said thin plate comprises a mesh comprising warp and weft, at least one of said warp and said weft comprising said shape memory alloy wires.

2. A splint as claimed in claim 1, said shape memory alloy wires consisting of a Ti-Ni series alloy exhibiting superelasticity at a normal or used temperature.

3. A splint as claimed in claim 2, said Ti-Ni series alloy having a martensite transformation start temperature not higher than a human body temperature after said Ti-Ni series alloy is subjected to a heat treatment at a temperature not lower than a recrystallization temperature of said alloy.

4. A splint as claimed in claim 3, said Ti-Ni series alloy exhibiting superelasticity at the human body temperature when said Ti-Ni series alloy is subjected to a heat treatment at a temperature between 400° C. and 500° C. after cold working at a rate of 30% or more.

5. A splint as claimed in claim 4, said mesh comprising blended woven fabric formed by a combination of said shape memory alloy wires and synthetic macromolecule wires.

6. A splint as claimed in claim 5, said synthetic macromolecule wires comprising at least one macromolecule selected from nylon, polyurethane, and polytetrafluoroethylen.

7. A splint as claimed in claim 6, one of said warp and said weft of said mesh comprising said shape memory alloy wires while the other comprises said synthetic macromolecule wires.

8. A splint as claimed in claim 4, said lamina or said thin plate comprising said mesh, both of said warp and said weft of said mesh comprising said shape memory alloy wires.

9. A splint as claimed in claim 8, said mesh of said lamina or said thin plate being coated with a synthetic resin material.

10. A splint as claimed in claim 9, said synthetic resin material being at least one selected from nylon, polyurethane, and polytetrafluoroethylene.

11. A supporter having a splint as claimed in claim 1.

12. Footwear having a splint as claimed in claim 1.

13. A foot correction method for reinforcement or correction of the foot in order to prevent and cure a deformity of said foot such as a flatfoot and hallux valgus, said method comprising the steps of preparing a lamina or a thin plate at least partially containing shape memory alloy wires, forming said lamina or said thin plate into a shape corresponding to a configuration of a desired part of said foot to be corrected, and attaching said lamina or said thin plate to said desired part, wherein said lamina or said thin plate comprises a mesh, said mesh comprising warp and weft, at least one of said warp and said weft comprising said shape memory alloy wires.

14. A foot correction method as claimed in claim 13, further comprising the step of repeating attachment and removal of said lamina or said thin plate.

15. A foot correction method as claimed in claim 13, further comprising the steps of raising a plantar arch by said lamina or said thin plate, and applying a pressure on either side of said foot, thereby maintaining a configuration of a longitudinal arch and a transversal arch of said foot so as to prevent and correct a spraying phenomenon of said foot.

16. A foot correction method as claimed in claim 13, said shape memory alloy wire consisting of a Ti-Ni series alloy exhibiting superelasticity at a normal or used temperature.

17. A foot correction method as claimed in claim 16, said Ti-Ni series alloy having a martensite transformation start temperature not higher than the human body temperature after said Ti-Ni series alloy is subjected to a heat treatment at a temperature not lower than a recrystallization temperature of said alloy.

18. A foot correction method as claimed in claim 17, said Ti-Ni series alloy exhibiting superelasticity at the human body temperature when said Ti-Ni series alloy is subjected to a heat treatment at a temperature between 400° C. and 500° C. after cold working at a rate of 30% or more.

19. A foot correction method as claimed in claim 18, said mesh comprising blended woven fabric formed by a combination of said shape memory alloy wires and synthetic macromolecule wires.

20. A foot correction method as claimed in claim 19, said synthetic macromolecule wires comprising at least one macromolecule selected from nylon, polyurethane, and polytetrafluoroethylene.

21. A foot correction method as claimed in claim 20, one of said warp and said weft of said mesh comprising said shape memory alloy wires while the other comprises said synthetic macromolecule wires.

22. A foot correction method as claimed in claim 18, said lamina or said thin plate comprising said mesh, both of said warp and said weft of said mesh comprising said shape memory alloy wires.

23. A foot correction method as claimed in claim 22, said mesh of said lamina or said thin plate being coated with a synthetic resin material.

24. A foot correction method as claimed in claim 23, said synthetic resin material being at least one selected from nylon, polyurethane, and polytetrafluoroethylene.

* * * * *